(12) United States Patent
Emerton et al.

(10) Patent No.: US 10,172,651 B2
(45) Date of Patent: Jan. 8, 2019

(54) CORTICAL BONE IMPLANT

(71) Applicant: Warsaw Orthopedic, Inc., Warsaw, IN (US)

(72) Inventors: Kelly Brook Emerton, Santa Rosa, CA (US); Susan J. Drapeau, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 933 days.

(21) Appl. No.: 13/660,434

(22) Filed: Oct. 25, 2012

(65) Prior Publication Data

US 2014/0121772 A1 May 1, 2014

(51) Int. Cl.
| | |
|---|---|
| *A61F 2/44* | (2006.01) |
| *A61B 17/70* | (2006.01) |
| *A61L 27/36* | (2006.01) |
| *A61L 27/54* | (2006.01) |
| *A61F 2/30* | (2006.01) |

(52) U.S. Cl.
CPC ........ *A61B 17/7064* (2013.01); *A61F 2/4405* (2013.01); *A61L 27/3608* (2013.01); *A61L 27/54* (2013.01); *A61F 2002/30059* (2013.01); *A61F 2002/30062* (2013.01); *A61F 2002/3097* (2013.01); *A61F 2002/3098* (2013.01); *A61F 2002/30957* (2013.01); *A61F 2002/30958* (2013.01); *A61F 2002/30967* (2013.01); *A61F 2002/30968* (2013.01); *A61F 2002/30971* (2013.01); *A61F 2002/30983* (2013.01); *A61F 2310/0097* (2013.01); *A61F 2310/00359* (2013.01); *A61F 2310/00796* (2013.01); *A61F 2310/00958* (2013.01); *A61F 2310/00976* (2013.01); *A61F 2310/00982* (2013.01); *A61L 2300/414* (2013.01); *A61L 2430/02* (2013.01)

(58) Field of Classification Search
CPC ............................ A61F 2/4644; A61F 2/4601
USPC ............................................. 623/17.11, 23.61
See application file for complete search history.

(56) References Cited

U.S. PATENT DOCUMENTS

| | | |
|---|---|---|
| 5,112,354 A | 5/1992 | Sires |
| 5,899,939 A | 5/1999 | Boyce et al. |
| 6,090,998 A | 7/2000 | Grooms et al. |
| 6,123,731 A | 9/2000 | Boyce et al. |
| 6,143,033 A | 11/2000 | Paul et al. |
| 6,162,225 A | 12/2000 | Gertzman et al. |
| 6,206,923 B1 | 3/2001 | Boyd et al. |
| 6,290,718 B1 | 9/2001 | Grooms et al. |
| D450,121 S | 11/2001 | Anderson |

(Continued)

FOREIGN PATENT DOCUMENTS

| | | |
|---|---|---|
| WO | 1996039203 A1 | 12/1996 |
| WO | 2000035511 A1 | 6/2000 |
| WO | 2001008714 A1 | 2/2001 |

*Primary Examiner* — David Isabella
*Assistant Examiner* — Christine Nelson (57) ABSTRACT

Bone implant compositions and methods are provide that have a first surface and a second surface, the first surface and the second surface comprising a demineralized bone matrix and having a plurality of perforations configured to receive demineralized bone; and a third surface of the bone implant comprising cortical bone, the third surface disposed between the first surface and the second surface. The bone implant compositions and methods provided are osteoinductive and allow rapid bone fusion.

13 Claims, 2 Drawing Sheets

(56) References Cited

U.S. PATENT DOCUMENTS

| | | |
|---|---|---|
| 6,340,477 B1 | 1/2002 | Anderson |
| D458,373 S | 6/2002 | Jackson |
| 6,409,765 B1 | 6/2002 | Bianchi et al. |
| 6,440,444 B2 * | 8/2002 | Boyce .................. A61F 2/28 424/422 |
| 6,454,811 B1 | 9/2002 | Sherwood et al. |
| 6,458,375 B1 | 10/2002 | Gertzman et al. |
| D467,341 S | 12/2002 | Meyer et al. |
| 6,530,955 B2 | 3/2003 | Boyle et al. |
| 6,547,823 B2 | 4/2003 | Scarborough et al. |
| 6,599,520 B2 | 7/2003 | Scarborough et al. |
| 6,616,698 B2 | 9/2003 | Scarborough |
| 6,730,124 B2 | 5/2004 | Steiner |
| 6,761,739 B2 | 7/2004 | Shepard |
| 6,827,720 B2 | 12/2004 | Leali |
| 6,855,167 B2 | 2/2005 | Shimp et al. |
| 6,902,578 B1 | 6/2005 | Anderson et al. |
| 7,001,551 B2 | 2/2006 | Meredith |
| 7,044,968 B1 | 5/2006 | Yaccarino, III et al. |
| 7,163,691 B2 | 1/2007 | Knaack et al. |
| 7,252,685 B2 | 8/2007 | Bindseil et al. |
| D553,742 S | 10/2007 | Park |
| D553,743 S | 10/2007 | Park |
| 7,323,011 B2 | 1/2008 | Shepard et al. |
| 7,323,193 B2 | 1/2008 | Morris et al. |
| D566,277 S | 4/2008 | Barry |
| 7,354,452 B2 | 4/2008 | Foley |
| 7,399,739 B2 | 7/2008 | Shimp |
| 7,413,576 B2 | 8/2008 | Sybert et al. |
| D580,551 S | 11/2008 | Cohen et al. |
| 7,491,237 B2 | 2/2009 | Randall et al. |
| 7,537,617 B2 | 5/2009 | Bindsell et al. |
| D595,853 S | 7/2009 | Hanson et al. |
| 7,563,284 B2 | 7/2009 | Coppes et al. |
| 7,645,458 B2 | 1/2010 | Shimp |
| 7,709,018 B2 | 5/2010 | Pastorello et al. |
| D619,255 S | 7/2010 | Richter et al. |
| 7,753,963 B2 | 7/2010 | Boyer, II et al. |
| 7,780,708 B2 | 8/2010 | Morris et al. |
| 7,833,245 B2 | 11/2010 | Kaes et al. |
| 7,837,740 B2 | 11/2010 | Semler et al. |
| 7,857,860 B2 | 12/2010 | Saini et al. |
| 7,931,692 B2 | 4/2011 | Sybert et al. |
| 7,988,733 B2 | 8/2011 | Shimp et al. |
| 8,007,533 B2 | 8/2011 | Zhukauskas et al. |
| 8,157,806 B2 | 4/2012 | Frigg et al. |
| 2002/0038123 A1 | 3/2002 | Visotsky et al. |
| 2003/0009235 A1 | 1/2003 | Manrique et al. |
| 2003/0055511 A1 | 3/2003 | Schryver et al. |
| 2003/0060825 A1 | 3/2003 | Alfaro et al. |
| 2003/0114936 A1 | 6/2003 | Sherwood et al. |
| 2003/0228288 A1 | 12/2003 | Scarborough et al. |
| 2004/0024457 A1 | 2/2004 | Boyce et al. |
| 2004/0115172 A1 | 6/2004 | Bianchi et al. |
| 2005/0015147 A1 | 1/2005 | Schwardt et al. |
| 2005/0065613 A1 | 3/2005 | Gross et al. |
| 2006/0015184 A1 | 1/2006 | Winterbottom et al. |
| 2006/0024656 A1 | 2/2006 | Morris et al. |
| 2006/0280803 A1 | 12/2006 | Kumar et al. |
| 2007/0073293 A1 | 3/2007 | Martz et al. |
| 2007/0088437 A1 | 4/2007 | Betz et al. |
| 2007/0098756 A1 | 5/2007 | Behnam |
| 2007/0154563 A1 | 7/2007 | Behnam et al. |
| 2008/0033572 A1 | 2/2008 | D'Antonio et al. |
| 2008/0058953 A1 | 3/2008 | Scarborough |
| 2008/0234822 A1 | 9/2008 | Govil et al. |
| 2009/0018659 A1 | 1/2009 | Malinin |
| 2009/0087471 A1 | 4/2009 | Shimp et al. |
| 2009/0099661 A1 * | 4/2009 | Bhattacharya ........ A61F 2/4455 623/17.16 |
| 2009/0130173 A1 | 5/2009 | Behnam et al. |
| 2009/0149893 A1 | 6/2009 | Semler et al. |
| 2009/0155378 A1 | 6/2009 | Behnam et al. |
| 2009/0227704 A1 | 9/2009 | Troxel et al. |
| 2010/0036413 A1 | 2/2010 | Nakaji |
| 2010/0049326 A1 | 2/2010 | Petersen et al. |
| 2010/0209470 A1 | 8/2010 | Mohan et al. |
| 2010/0274355 A1 | 10/2010 | McGuire et al. |
| 2011/0045044 A1 | 2/2011 | Masinaei et al. |
| 2011/0066241 A1 | 3/2011 | Nauman et al. |
| 2011/0118850 A1 | 5/2011 | Govil et al. |
| 2011/0144766 A1 | 6/2011 | Kale et al. |
| 2011/0182963 A1 | 7/2011 | McKay |
| 2012/0010659 A1 | 1/2012 | Angert et al. |
| 2013/0282138 A1 * | 10/2013 | McKay ............... A61B 17/7062 623/23.61 |
| 2014/0031937 A1 * | 1/2014 | McKay ................. A61F 2/4455 623/17.16 |

\* cited by examiner

CORTICAL BONE IMPLANT

BACKGROUND

The rapid and effective repair of bone defects caused by injury, disease, wounds, or surgery is a goal of orthopedic surgery. Toward this end, a number of bone implants have been used or proposed for use in the repair of bone defects. The biological, physical, and mechanical properties of the bone implants are among the major factors influencing their suitability and performance in various orthopedic applications.

Bone implants are used to repair bone that has been damaged by disease, trauma, or surgery. Bone implants may be utilized when healing is impaired in the presence of certain drugs or in disease states such as diabetes, when a large amount of bone or disc material is removed during surgery, or when bone fusion is needed to create stability. In some types of spinal fusion, for example, bone implants are used to replace the cushioning disc material between the vertebrae or to repair a degenerative facet joint.

One type of bone implant is the bone graft. Typically, bone graft (e.g., osteograft) materials may include both synthetic and natural bone. Natural bone may be taken from the graft recipient (autograft) or may be taken from another source (allograft), such as a cadaver, or (xenograft), such as bovine. Autografts have advantages such as decreased immunogenicity and greater osteoinductive potential, but there can also be problems with donor site morbidity and limited supply of suitable bone for grafting. On the other hand, allografts are available in greater supply and can be stored for years. However, allografts tend to be less osteoinductive.

Osteoconduction and osteoinduction both contribute to bone formation. A graft material is osteoconductive if it provides a structural framework or microscopic and macroscopic scaffolding for cells and cellular materials that are involved in bone formation (e.g., osteoclasts, osteoblasts, vasculature, mesenchymal cells).

Osteoinductive material, on the other hand, stimulates differentiation of host mesenchymal cells into chondroblasts and osteoblasts. Natural bone allograft materials can comprise either cortical or cancellous bone. A distinguishing feature of cancellous bone is its high level of porosity relative to that of cortical bone, providing more free surfaces and more of the cellular constituents that are retained on these surfaces. It provides both an osteoinductive and osteoconductive graft material, but generally does not have significant load-bearing capacity. Optimal enhancement of bone formation is generally thought to require a minimum threshold quantity of cancellous bone, however. Cortical (compact) bone has greater strength or load-bearing capacity than cancellous bone, but is less osteoconductive. In humans for example, only approximately twenty percent of large cortical allografts are completely incorporated at five years. Delayed or incomplete incorporation may allow micromotion, leading to host bone resorption around the allograft. A more optimal bone graft material would combine significant load-bearing capacity with both osteoinductive and osteoconductive properties, and much effort has been directed toward developing such a graft material.

Some allografts comprise mammalian cadaver bone treated to remove all soft tissue, including marrow and blood, and then textured to form a multiplicity of holes of selected size, spacing, and depth. The textured bone section is then immersed and demineralized, for example, in a dilute acid bath. Demineralizing the bone exposes osteoinductive factors, but extensive demineralization of bone also decreases its mechanical strength.

Allografts have also been formed of organic bone matrix with perforations that extend from one surface, through the matrix, to the other surface to provide continuous channels between opposite surfaces. The organic bone matrix is produced by partial or complete demineralization of natural bone. Although the perforations increase the scaffolding potential of the graft material and may be filled with osteoinductive material as well, perforating organic bone matrix through the entire diameter of the graft decreases its load-bearing capacity.

Partially-demineralized cortical bone constructs may be surface-demineralized to prepare the graft to be soaked in bone growth-promoting substances such as bone morphogenetic protein (BMP). Although this design allows greater exposure of the surrounding tissue to growth-promoting factors, the surface demineralization necessary to adhere a substantial amount of growth-promoting factors to the graft material decreases the allograft's mechanical strength.

What is needed is a bone implant that combines the osteoinductive and osteoconductive properties of cancellous bone with the load-bearing capacity provided by cortical allograft materials. Compositions and methods are needed that facilitate bone remodeling and new bone growth, and integration of the bone implant (e.g., allograft) into host bone.

SUMMARY

Compositions and methods are provided that facilitate bone remodeling and new bone growth, and integration of the bone implant (e.g., allograft) into host bone. In some embodiments, the bone implant provides an improved surface between the dense cortical allograft and a patient's host bone to facilitate incorporation of the allograft construct and fusion to host bone. In some embodiments, at least a portion of the bone implant comprises cortical allograft and at least a portion that contains osteoinductive demineralized bone matrix material on its surface to initiate the bone fusion process at the bone allograft surface interface and provide rapid bone bonding to the demineralized surface of the cortical allograft. The bone implant of the current application, in some embodiments, is load bearing and provides good mechanical strength.

In some embodiments, there is a bone implant comprising a first surface and a second surface, the first surface and the second surface having a plurality of perforations, the first surface and the second surface comprising demineralized bone matrix material; and a third surface of the bone implant comprising nondemineralized cortical bone, wherein the third surface is disposed between the first surface and the second surface.

In some embodiments, a bone implant is provided that is configured for repairing a facet joint defect, the bone implant comprising a first surface and a second surface, the first surface and the second surface comprising a demineralized bone matrix material and having a plurality of perforations configured to receive bone material therein; and a third surface of the bone implant comprising nondemineralized cortical bone, wherein the third surface is disposed between the first surface and the second surface.

In some embodiments, there is an allograft configured for repairing a facet joint defect comprising a first surface and a second surface comprising a demineralized bone matrix material and having a plurality of perforations having demineralized bone disposed therein; and an third surface of the allograft comprising nondemineralized cortical bone, wherein the third surface is disposed between the first surface and the second surface.

In some embodiments, there is a method for repairing a facet joint defect in a patient in need of such treatment, the method comprising inserting an allograft into the facet joint defect, the allograft comprising a first surface and a second surface having a plurality of perforations having demineralized bone disposed therein, the first surface and the second surface comprising a demineralized bone matrix material; and a third surface of the allograft comprising nondemineralized cortical bone, wherein the third surface is disposed between the first surface and the second surface.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "an allograft" includes one, two, three or more allografts.

The term "biodegradable" includes that all or parts of the carrier and/or implant will degrade over time by the action of enzymes, by hydrolytic action and/or by other similar mechanisms in the human body. In various embodiments, "biodegradable" includes that the carrier and/or implant can break down or degrade within the body to non-toxic components after or while a therapeutic agent has been or is being released. By "bioerodible" it is meant that the carrier and/or implant will erode or degrade over time due, at least in part, to contact with substances found in the surrounding tissue, fluids or by cellular action. By "bioabsorbable" or "bioresorbable" it is meant that the carrier and/or implant will be broken down and absorbed within the human body, for example, by a cell or tissue. "Biocompatible" means that the allograft will not cause substantial tissue irritation or necrosis at the target tissue site.

The term "mammal" refers to organisms from the taxonomy class "mammalian," including but not limited to humans, other primates such as chimpanzees, apes, orangutans and monkeys, rats, mice, cats, dogs, cows, horses, etc.

"A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the implant is designed for immediate release. In other embodiments the implant is designed for sustained release. In other embodiments, the implant comprises one or more immediate release surfaces and one or more sustained release surfaces.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or corticocancellous of autogenous, allogenic, xenogenic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "osteoimplant," as used herein, refers to any bone-derived implant prepared in accordance with the embodiments of this disclosure and therefore is intended to include expressions such as bone membrane, bone graft, etc.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "xenograft" refers to tissue or organs from an individual of one species transplanted into or grafted onto an organism of another species, genus, or family.

The term "demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized." In some embodiments, part or all of the surface of the bone can be demineralized. For example, part or all of the surface of the allograft can be demineralized to a depth of from about 100 to about 5000 microns, or about 150 microns to about 1000 microns. If desired, the outer surface of the intervertebral implant can be masked with an acid resistant coating or otherwise treated to selectively demineralize unmasked portions of the outer surface of the intervertebral implant so that the surface demineralization is at discrete positions on the implant.

The term "demineralized bone matrix," as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the disclosure.

The term "superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The terms "pulverized bone", "powdered bone" or "bone powder" as used herein, refers to bone particles of a wide range of average particle size ranging from relatively fine powders to coarse grains and even larger chips.

The allograft can comprise bone fibers. Fibers include bone elements whose average length to average thickness ratio or aspect ratio of the fiber is from about 50:1 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are preferably demineralized however some of the original mineral content may be retained when desirable for a particular embodiment.

Non-fibrous, as used herein, refers to elements that have an average width substantially larger than the average thickness of the fibrous bone element or aspect ratio of less than from about 50:1 to about 1000:1. In some embodiments, the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular".

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Demineralized Bone Allograft

Compositions and methods are provided that facilitate bone remodeling and new bone growth, and integration of the bone implant (e.g., allograft) into host bone. In some embodiments, the bone implant provides an improved surface between the dense cortical allograft and a patient's host bone to facilitate incorporation of the allograft construct and fusion to host bone. In some embodiments, the bone implant comprises a cortical allograft that contains osteoinductive demineralized bone matrix material on its surface to initiate the bone fusion process at the bone allograft surface interface and provide rapid bone bonding to the demineralized surface of the cortical allograft. The bone implant of the current application, in some embodiments, is load bearing and provides good mechanical strength.

In some embodiments, a bone implant is provided comprising a first surface and a second surface, the first surface and the second surface comprising a demineralized bone matrix material and having a plurality of perforations configured to receive a bone material therein; and a third surface of the bone implant comprising nondemineralized cortical bone, wherein the third surface is disposed between the first surface and the second surface.

In some embodiments, the bone implant is a structural cortical H-shaped graft for placement between the spinous process. The graft provides structural support between the processes as well as providing a cover for bony defects created during decompression procedures. In one embodiment, the bone implant is configured for disposal in a facet joint. In some embodiments, the bone implant comprises a first surface and a second surface that define wing shaped ends that are demineralized with a plurality of perforations. In one embodiment, the plurality of perforations increase the surface area of the implant to decrease demineralization time. In some embodiments, at least two drilled holes are added to the bone graft to facilitate delivery via instrumentation into the graft surgical site. In some embodiments, the implant can be sterilized via various sterilization procedures. In some embodiments, the bone implant is sterilized.

In some embodiments, the bone implant comprises segmented demineralized sections and a plurality of perforated sections. In some embodiments, the body of the graft will not be demineralized. This non-demineralized body provides structural support between the processes as well as providing cover for defects created during decompression. In some embodiments, the bone implant comprises a first surface and a second surface that define demineralized wing shaped ends configured to increase bone fusion due to exposure of the surface area with exposed native bone proteins. In some embodiments, the wings have a plurality of complete perforations to increase the surface area for bone protein exposure and to decrease demineralization time.

In some embodiments, the bone implant comprises a structural allograft that can be implanted between a dense cortical allograft and a patients' host bone to facilitate incorporation of the allograft construct and fusion to host bone. In this embodiment, this allograft can comprise surfaces of demineralized bone and then a surface that comprises non-demineralized cortical bone. In one embodiment, the demineralized surfaces are surface demineralized and then coated with a demineralized powder. The bone implant will provide a therapeutic amount of osteoinductive DBM material to initiate the fusion process at the interface and rapid bone bonding to the surface demineralized cortical allograft.

Current structural allograft implants can be made from dense cortical bone requiring significant time for the host bone to remodel the allograft interface surface via osteoclastic resorption and eventual deposition of new bone into cutting cones into the allograft. By employing the bone implant of the current application that includes surface demineralized bone material, the fusion process can be accelerated.

In some embodiments, the composite implant is configured to increase the surface area contact of the allograft with the host bone, which will result in faster fusion and incorporation of the composite implant into host bone and ultimately a stronger fusion mass. In some embodiments, the allograft bone used in the implant is surface demineralization to increase its osteoinductivity and fusion with the host bone. In some embodiments, the implant is designed so that the majority of the mechanical load is carried by the allograft that comprises cortical bone. This, typically, is in the center of the implant and away from the surfaces that have perforations and/or are demineralized. Surfaces that have perforations or are demineralized will have more flexibility that allows easier implantation.

In some embodiments, the portion of the allograft that is not demineralized comprises load bearing and/or higher compressive strength allograft material. In some embodiments, the portion of the allograft that is not load bearing comprises demineralized bone material that also has a low compressive strength.

In some embodiments, the implant device contacts host bone and the implant device comprises from about 1% to about 30% or from about 5% to about 25% by weight of demineralized bone material.

In some embodiments, the bone allograft material comprises demineralized bone matrix fibers and demineralized bone matrix powder in a ratio of 25:75 to about 75:25 fibers to chips.

In some embodiments, the surface demineralization provides a more conducive surface for the demineralized bone to attach to via both friction and cohesive binding of collagen/protein compositions to the allograft. The healing process also exposes some of the inherent bone growth factors in the cortical allograft material to further facilitate remodeling and new bone formation. The surface demineralization of the allograft and/or DBM powder and/or fiber provides an easier route of entry for bone remodeling to occur in the cortical allograft bone further facilitating faster fusion.

Demineralized bone matrix (DBM) is demineralized allograft bone with osteoinductive activity. DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (e.g. glycerol or a polymer). DBM is mostly an osteoinductive product, but lacks enough induction to be used on its own in challenging healing environments such as posterolateral spine fusion.

Various designs are contemplated. The surface demineralization can be strategically located and depth varied to optimize the incorporation process. For example it could be limited to certain areas on the interface so as not to lead to allograft subsidence. Alternatively it could be limited to the inner and outer surfaces to preferentially facilitate allograft incorporation to those surfaces first. For example, part or all of the surface of the allograft can be demineralized to a depth of from about 50 to about 5000 microns, or about 100 microns to about 1000 microns or about 2000 microns. If desired, the outer surface of the intervertebral implant can be masked with an acid resistant coating or otherwise treated to selectively demineralize unmasked portions of the outer surface of the intervertebral implant so that the surface demineralization is at discrete positions on the implant.

Regarding coating with demineralized bone, it too can be strategically located and depth varied to optimize the incorporation process. For example it could be limited to friction groves in the surfaces comprising demineralized bone so a thicker coating can be applied to accelerate new bone formation. One embodiment includes the use of a plurality of perforations filled with DBM since osteoblast preferentially attached to concave surfaces and this is where bone formation typically occurs first. Alternatively it could be limited to the first and second surfaces to preferentially facilitate allograft incorporation to those surfaces first. The DBM is applied to the surface demineralized surface and allowed to bind via air drying, or alternatively freeze dried, heat drying, or a mild chemical crosslinking agent or adhesive can be used. The form of the DBM is can be chips, shards, powders, fibers or a combination thereof, which are osteoinductive. These can be filled into the plurality of perforations of the allograft or one or more of them can be disposed on the allograft surface. Therefore, in some embodiments, the allograft can have both surface demineralization and DBM chips, shards, powders, or a combination thereof disposed on its surface and/or in the plurality of perforations.

In one embodiment, DBM powder can range in average particle size from about 0.0001 to about 1.2 cm and from about 0.002 to about 1 cm. The bone powder can be obtained from cortical, cancellous and/or corticocancellous allogenic or xenogenic bone tissue. In general, allogenic bone tissue is preferred as the source of the bone powder.

In some embodiments, the coating thickness of DBM powder and/or fibers may be thin, for example, from about 5, 10, 15, 20, 25, 30, 35, 40, 45 or 50 microns to thicker coatings 60, 65, 70, 75, 80, 85, 90, 95, 100 microns. In some embodiments, the range of the coating ranges from about 5 microns to about 250 microns or 5 microns to about 200 microns.

According to some embodiments of the disclosure, the demineralized bone matrix may comprise demineralized bone matrix fibers and/or demineralized bone matrix chips. In some embodiments, the demineralized bone matrix may comprise demineralized bone matrix fibers and demineralized bone matrix chips in a 30:60 ratio. According to one embodiment of the disclosure, the bone composite comprises a bone powder, a polymer and a demineralized bone. In different embodiments of the disclosure, bone powder content can range from about 5% to about 90% w/w, polymer content can range from about 5% to about 90% w/w, and demineralized bone particles content comprises the reminder of the composition. Preferably, the demineralized bone particles comprise from about 20% to about 40% w/w while the polymer and the bone powder comprise each from about 20% to about 60% w/w of the composition. The bone graft materials of the present disclosure include those structures that have been modified in such a way that the original chemical forces naturally present have been altered to attract and bind molecules, including, without limitation, growth factors and/or cells, including cultured cells.

Namely, the demineralized allograft bone material may be further modified such that the original chemical forces naturally present have been altered to attract and bind growth factors, other proteins and cells affecting osteogenesis, osteoconduction and osteoinduction. For example, a demineralized allograft bone material may be modified to provide an ionic gradient to produce a modified demineralized allograft bone material, such that implanting the modified demineralized allograft bone material results in enhanced ingrowth of host bone.

In one embodiment an ionic force change agent may be applied to modify the demineralized allograft bone material. The demineralized allograft bone material may comprise, e.g., a demineralized bone matrix (DBM) comprising fibers, particles and any combination of thereof. According to another embodiment, a bone graft structure may be used which comprises a composite bone, which includes a bone powder, a polymer and a demineralized bone.

The ionic force change agent may be applied to the entire demineralized allograft bone material or to selected portions/surfaces thereof.

The ionic force change agent may be a binding agent, which modifies the demineralized allograft bone material or bone graft structure to bind molecules, such as, for example, DBM, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7(OP-1), rhBMP-7, GDF-5, LIM mineralization protein, platelet derived growth factor (PDGF), transforming growth factor-β (TGF-β), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

An adhesive may be applied to the DBM powders and/or fibers. The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (e.g., hydroxypropylcellulose). In some embodiments, the synthetic polymers having a carboxyl group, may comprise poly(acrylic acid), poly(methacrylic acid), poly(vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyl-disulfide, maleimide, aldehyde, iodoacetamide or a combination thereof. In some embodiments, the adhesive material can comprise at least one of fibrin, a cyanoacrylate (e.g., N-butyl-2-cyanoacrylate, 2-octyl-cyanoacrylate, etc.), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers as mentioned in U.S. Pat. No. 4,708,821. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site, cannula and/or expandable member. In some embodiments, to have the device adhere to the target tissue site, pressure is applied in a direction substantially perpendicular to a surgical incision.

Multi-component adhesives harden by mixing two or more components, which chemically react. This reaction causes polymers to cross-link into acrylics, urethanes, and/or epoxies. There are several commercial combinations of multi-component adhesives in use in industry. Some of these combinations are: polyester resin-polyurethane resin; polyols-polyurethane resin, acrylic polymers-polyurethane resins or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied (e.g., body heat), the components react and cross-link. This type of adhesive includes epoxies, urethanes, and/or polyimides. The adhesive can be a moisture curing adhesive that cures when it reacts with moisture present (e.g., bodily fluid) on the substrate surface or in the air. This type of adhesive includes cyanoacrylates or urethanes. The adhesive can have natural components, such as for example, vegetable matter, starch (dextrin), natural resins or from animals e.g. casein or animal glue. The adhesive can have synthetic components based on elastomers, thermoplastics, emulsions, and/or thermosets including epoxy, polyurethane, cyanoacrylate, or acrylic polymers.

The allograft provides a matrix for the cells to guide the process of tissue formation in vivo in three dimensions. The morphology of the allograft guides cell migration and cells are able to migrate into or over the allograft, respectively. The cells then are able to proliferate and synthesize new tissue and form bone and/or cartilage. In some embodiments, one or more allografts are stacked on one or more biodegradable carriers.

In some embodiments, the allograft comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the allograft has a porosity of at least about 30%, at least about 50%, at least about 60%, at least about 70%, at least about 90%. The pore may support ingrowth of cells, formation or remodeling of bone, cartilage and/or vascular tissue.

The allograft in addition to bone and/or demineralized bone may comprise natural and/or synthetic material. For example, the allograft may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, or combinations thereof.

In some embodiments, the allograft may comprise a resorbable ceramic (e.g., hydroxyapatite, tricalcium phosphate, bioglasses, calcium sulfate, etc.) tyrosine-derived polycarbonate poly(DTE-co-DT carbonate), in which the pendant group via the tyrosine—an amino acid—is either an ethyl ester (DTE) or free carboxylate (DT) or combinations thereof.

In some embodiments, the allograft may comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the allograft may be seeded with harvested bone cells and/or bone tissue, such as for example, cortical bone, autogenous bone, allogenic bones and/or xenogenic bone. In some embodiments, the allograft may be seeded with harvested cartilage cells and/or cartilage tissue (e.g., autogenous, allogenic, and/or xenogenic cartilage tissue). For example, before insertion into the target tissue site, the allograft can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the allograft provided, and the allograft may be kneaded by hand, thereby obtaining a pliable consistency that may subsequently be packed into the osteochondral defect.

The allograft may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the allograft has a density of between about 1.6 g/cm$^3$, and about 0.05 g/cm$^3$. In some embodiments, the allograft has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the allograft may be tailored to the site at which it is to be situated. For example, it may be in the shape of a morsel, a plug, a pin, a peg, a cylinder, a block, a wedge, ring, a sheet, etc. In some embodiments, the allograft is H-shaped for placement between the spinous process.

In some embodiments, the allograft may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent may be disposed on or in the allograft by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the allograft.

In some embodiments, the allograft may comprise sterile and/or preservative free material.

In applying the allograft to the bone defect, the bone defect site in need of treatment will be surgically prepared for receipt of the allograft. This preparation can include excision of bone at the site to create a hole or void in which the allograft will be received. Tissue removal can be conducted in any suitable manner including for instance drilling and/or punching, typically in a direction substantially perpendicular to the bone defect site, to create a recipient hole or void having a depth approximating that of the allograft to be implanted.

In some embodiments, the depth of the allograft can be for example, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm.

In some embodiments, the opening for receiving the allograft will be created using a drill or punch having a circular cross-section. In some embodiments, multiple, overlapping passes with the drill or punch can be made, in order to create an opening having a cross-section defined by multiple, intersecting circular arcs. A chisel can then be used to shape the recipient hole to receive the osteochondral implant.

In some embodiments, the allograft can include DBM particles, and/or cells (e.g., bone, chondrogenic cells and/or tissue) seeded or attached to it.

In some embodiments, a small amount of biologic glue can be applied into the hole or used to attached the DBM particles to the allograft, which is also surface demineralized. Suitable organic glues include TISSEEL® or TISSUCOL® (fibrin based adhesive; Immuno AG, Austria), Adhesive Protein (Sigma Chemical, USA), Dow Corning Medical Adhesive B (Dow Corning, USA), fibrinogen thrombin, elastin, collagen, alginate, demineralized bone matrix, casein, albumin, keratin or the like. A composite fibrin glue can be mixed with milled cartilage from for example, a bovine fibrinogen (e.g., SIGMA F-8630), thrombin (e.g., SIGMA T-4648) and aprotinin (e.g., SIGMA A6012. Also, human derived fibrinogen, thrombin and aprotinin can be used.

In some embodiments, a method for repairing a bone defect, such as, for example, a facet joint defect, in a patient in need of such treatment is provided, the method comprising inserting an allograft into the facet joint defect, the allograft comprising a first surface and a second surface comprising a demineralized bone matrix material, the first and second surfaces comprising a plurality of perforations that have demineralized bone therein; and a third surface of the allograft comprising nondemineralized cortical bone, wherein the third surface is disposed between the first surface and the second surface.

In some embodiments, a method for repairing a bone defect is provided where the method comprises forming a hole at or near the bone defect and inserting the allograft into the bone defect, wherein the cavity is completely filled with demineralized bone powder or demineralized bone fibers.

Figure 1:
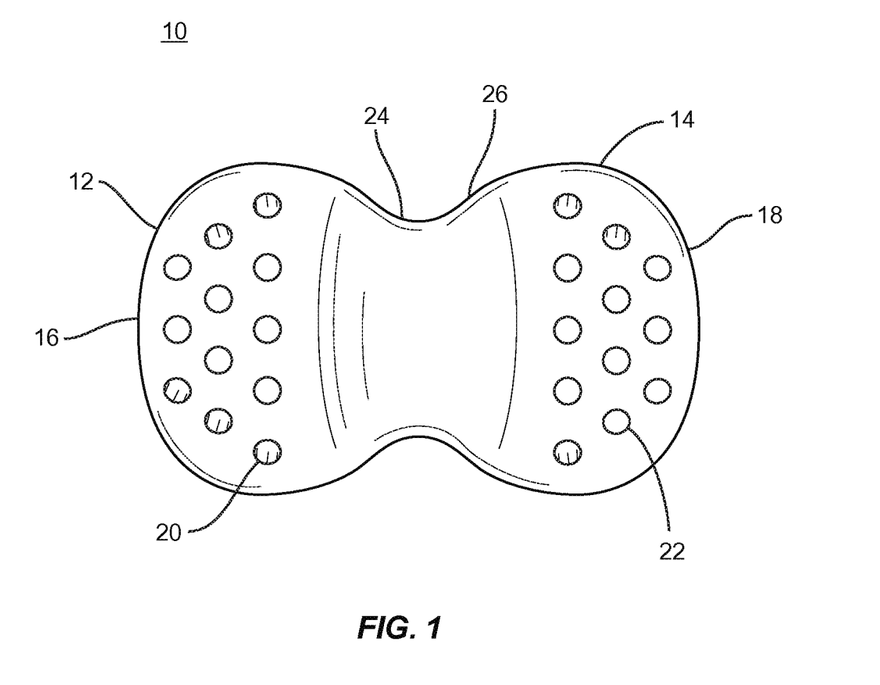
FIG. 1 illustrates a front view of an embodiment of a bone implant that has a first surface and a second surface comprising a demineralized bone matrix. The first surface and the second surface comprise a plurality of perforations disposed at discrete positions about the surfaces containing demineralized bone. The bone implant comprises a third surface that comprises nondemineralized cortical bone. The third surface is disposed between the first surface and the second surface.

Now referring to the figure, FIG. 1 illustrates a front view of an embodiment of a bone implant device, allograft 10 is shown that has a first surface 12 and a second surface 14. This type of implant can be configured for insertion between intervertebral discs, and/or for repair of the facet joint. Surfaces 12, 14 comprise a first wing 16 and a second wing 18 respectively. Allograft 10 includes a plurality of perforations 20 disposed in a uniform or discrete arrangement throughout surfaces 12, 14. Perforations 20 can also be configured for engagement with a bone graft instrument. The term 'perforations' includes and encompasses voids, apertures, bores, depressions, holes, indentations, grooves, channels, notches, cavities or the like.

In some embodiments, perforations 20 are disposed in a honeycomb configuration. In some embodiments, perforations 20 may be provided in any of a variety of shapes in addition to the generally circular shape shown, including but not limited to generally rectangular, oblong, curved, triangular and other polygonal or non-polygonal shapes. For example, each perforation can comprise a shape that is triangular, pyramidal, square, rectangular, pentagonal, hexagonal, heptagonal, octagonal, U-shaped, V-shaped, W-shaped, concave, crescent, or a combination thereof.

In some embodiments, perforations 20 comprise about less than 50% of the entire graft 10. In some embodiments, perforations comprise about less than 33% of the entire graft. In some embodiments, perforations 20 comprise about less than 66% of the entire graft. In some embodiments, perforations 20 comprise about less than 75% of the entire graft.

Perforations 20 contact host bone with a demineralized bone portion containing demineralized bone powder, fibers, shards, chips, or the like 22. The demineralized bone powder can be coated in or on the perforations using a suitable adhesive, glue, binder, carrier, or in some embodiments, the demineralized bone powder can be agglomerated and packed into perforations 20.

The surface of the perforations 20 can, in some embodiments, be surface demineralized. In some embodiments, the perforations 20 can be configured to mate with a corresponding mating surface in host bone. This corresponding mating surface in host bone, in some embodiments, can be made in host bone, by for example, drilling, etching, chiseling, or other device. Allograft 10 includes a third surface 24 comprising nondemineralized cortical bone. Surface 24 is disposed between surfaces 12, 14. In some embodiments, surface 24 comprises fully mineralized cortical bone and has the highest compressive strength of the allograft in some embodiments an outer surface 26 comprises demineralized cortical bone and is configured for engagement with a defect site.

It will be understood by those of ordinary skill in the art that the demineralized surfaces will have lower compressive strength and more flexibility than the nondemineralized regions. In this way, the implant can be easily inserted at the target site and positioned so that the load bearing forces will be directed on the non-demineralized surfaces of the implant.

Figure 2:
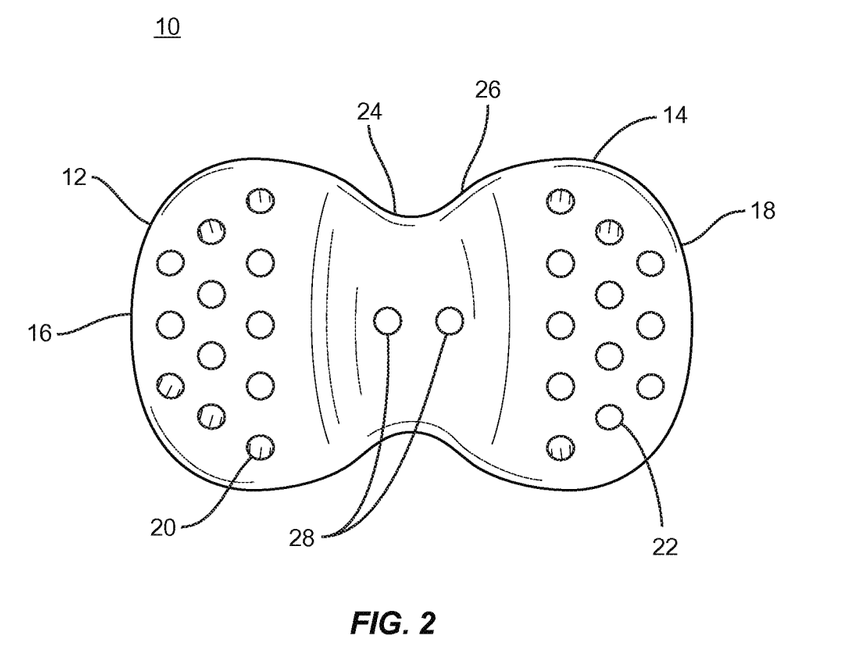
FIG. 2 illustrates a front view of an embodiment of a bone implant that has a first surface and a second surface comprising a demineralized bone matrix. The first surface and the second surface comprise a plurality of perforations disposed at discrete positions about the surfaces containing demineralized bone. The bone implant comprises a third surface that comprises nondemineralized cortical bone. The third surface is disposed between the first surface and the second surface.

FIG. 2 illustrates a front view of an embodiment of a bone implant device. Allograft 10 includes at least two drilled holes 28. In some embodiments, holes 28 are drilled in the nondemineralized cortical portion, surface 24 of allograft 10. In some embodiments, holes 28 are drilled in the demineralized bone surfaces 12, 14. In some embodiments, holes 28 are drilled in surfaces 12, 14 and 24. Holes 28 are configured for engagement with individual or incorporated biocompatible inorganic attachment members.

In some embodiments, allograft 10 can be combined with a spinal implant, such as, for example, bone fasteners, clips, plates, cages and/or other allograft materials. In some embodiments, allograft 10 is stackable. Thus, holes 28 can be aligned with other implants, and a plurality of implants can be stacked on each other.

In some embodiments, the depth of the demineralized region of the allograft of FIG. 2 varies throughout the allograft. In some embodiments, the first surface and the second surface of the allograft is selectively demineralized so as to avoid subsidence when the bone implant is implanted into a host bone of a patient. In FIG. 2, the perforations 20 and 22 can be in a demineralized surface. Edges 16 and 18 of the implant can be placed adjacent to host bone. In FIG. 2, zone 26 is also another fully mineralized zone of allograft bone.

In some embodiments, the demineralized bone powder, fiber, shards, and/or chips can be attached to the cavity by drying, freeze drying, heat drying, or using a chemical crosslinking agent.

In some embodiments, the perforations are predrilled and are partially or completely filled with plugs or inserts that are demineralized, or surface demineralized. In some embodiments, the plugs or inserts comprise cortical bone that is surface demineralized and then the plug or insert is friction fit or placed into the perforation of the implant, the plug or insert stays in place by friction.

In some embodiments, the perforations can be drilled into the implant or surrounding bone and then the demineralized plug or insert implanted into the prepared perforation. In some embodiments, the plugs or inserts stay in the perforations easier if the plugs or insert are cored from freeze dried demineralized bone and then press-fit rather than coring undemineralized or fully mineralized bone plugs or inserts, demineralizing them, press-fitting into the perforations and freeze drying the complete bone implant. Freeze drying causes the demineralized plugs to shrink and fall out of the perforations. In some embodiments, the demineralized plug or insert is flush with the bone implant. In some embodiments, the demineralized plug or insert protrudes from the bone implant. In some embodiments, the demineralized plug or insert is not flush with the bone implant, but is below its surface.

In some embodiments, the bone implant is designed to optimize contact of the demineralized bone with the host bone.

In some embodiments, the shape of the demineralized bone plug or insert may be tailored to the site at which it is to be situated. For example, it may be in the shape of a morsel, a plug, a pin, a peg, a cylinder, a block, a wedge, a sheet, etc. that can be implanted into the cortical bone implant, which itself can be surface demineralized.

In one embodiment, the implant comprises creases that allow the bone implant to be folded to place the implant at or in the bone defect. All or portions of the allograft can comprise a therapeutic agent disposed in or on the allograft. In some embodiments, the creases comprise a therapeutic agent that when folded in, on or around the bone defect, the creases release the therapeutic agent.

The bone implant device may also include mechanisms or features for reducing and/or preventing slippage or migration of the device during insertion. For example, one or more surfaces of the implant may include projections such as ridges or teeth (not shown) for increasing the friction between the implant and the adjacent contacting surfaces of the bone so to prevent movement of the implant after introduction to a desired location.

According to some embodiments, fusion may be facilitated or augmented by introducing or positioning various osteoinductive materials within the cavities in the implant device. Such osteoinductive materials may be introduced before, during, or after insertion of the exemplary implant device, and may include (but are not necessarily limited to) autologous bone harvested from the patient receiving the implant device, bone allograft, bone xenograft, any number of non-bone implants (e.g. ceramic, metallic, polymer), bone morphogenic protein, and/or bio-resorbable compositions.

In some embodiments, the bone implant may comprise an allograft portion that is configured to be joined to another allograft portion or a non-allograft portion comprising a polymer. In this way, the implant can be joined before it is implanted at or near the target site. The implant can have mating surfaces comprising recesses and/or projections and reciprocating recesses and/or projections (e.g., joints) that allow the implant to be assembled before implantation. Assembly can also include, for example, use of an adhesive material to join parts of the implant together and provide strong interlocking fit.

Growth Factors

In some embodiments, a growth factor and/or therapeutic agent may be disposed on or in the allograft by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the allograft by the surgeon before the allograft is administered or it may be available from the manufacturer beforehand.

The allograft may comprise at least one growth factor. These growth factors include osteoinductive agents (e.g., agents that cause new bone growth in an area where there was none) and/or osteoconductive agents (e.g., agents that cause in growth of cells into and/or through the allograft). Osteoinductive agents can be polypeptides or polynucleotides compositions. Polynucleotide compositions of the osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art, (See, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Preferred embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within carrier are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta genes ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), TP508 (an angiogenic tissue repair peptide), as well as mixtures or combinations thereof.

In another embodiment, the one or more isolated osteoinductive agents useful in the bioactive formulation are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and or combination thereof; Osteoprotegerin; TGF-beta-1, TGF-beta-2, TGF-beta-3, or any combination thereof; or any combination of one or more members of these groups.

The concentrations of growth factor can be varied based on the desired length or degree of osteogenic effects desired. Similarly, one of skill in the art will understand that the duration of sustained release of the growth factor can be modified by the manipulation of the compositions comprising the sustained release formulation, such as for example, modifying the percent of allograft found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that simulate the natural healing process.

In some embodiments, a statin may be used as the growth factor. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appin. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

The amount of growth factor, e.g., bone morphogenic protein may be sufficient to cause bone and/or cartilage growth. In some embodiments, the growth factor is rhBMP-2 and is contained in one or more carriers in an amount of from 0.05 to 2 mg per cubic centimeter of the biodegradable carrier. In some embodiments, the amount of rhBMP-2 morphogenic protein is from 2.0 to 2.5 mg per cubic centimeter (cc) of the biodegradable carrier.

In some embodiments, the growth factor is supplied in an aqueous buffered solution. Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

In some embodiments, the BMP-2 is provided in a vehicle (including a buffer) containing sucrose, glycine, L-glutamic acid, sodium chloride, and/or polysorbate 80.

Additional Therapeutic Agents

The growth factors of the present application may be disposed on or in the allograft and/or carrier with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In various embodiments, a kit is provided that may include additional parts along with the allograft to be used to implant the allograft. The kit may include the allograft in a first compartment. The second compartment may include a biodegradable carrier and the growth factor and any other instruments needed for the implanting the osteochondral implant. A third compartment may include gloves, drapes, wound dressings and other procedural supplies for maintaining sterility during the implanting process, as well as an instruction booklet. A fourth compartment may include additional tools for implantation (e.g., drills, drill bits, bores, punches, etc.). Each tool may be separately packaged in a plastic pouch that is radiation sterilized. A fifth compartment may comprise an agent for radiographic imaging or the agent may be disposed on the allograft and/or carrier to monitor placement and tissue growth. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A bone implant comprising a first surface and a second surface comprising a demineralized bone matrix, the first surface and the second surface comprising a plurality of perforations configured to receive a bone material and to increase the surface area of the bone implant; and a third surface facing the same direction as the first surface and the second surface of the bone implant comprising nondemineralized cortical bone, wherein the third surface is disposed between the first surface and the second surface, and the bone implant comprises a top surface and a bottom surface, the perforations extending from the top surface, through the demineralized bone matrix, to the bottom surface to provide channels between the top and the bottom surfaces; and the third surface of the nondemineralized cortical bone does not contain any perforations, wherein the top and the bottom surfaces comprise the first, the second and the third surfaces.

2. A bone implant according to claim 1, wherein the first surface defines a first wing and the second surface defines a second wing.

3. A bone implant according to claim 2, wherein the first wing and the second wing have a concave configuration at the third surface.

4. A bone implant according to claim 1, wherein the perforations comprise (i) a coating of demineralized matrix material disposed therein; (ii) demineralized bone powder or demineralized bone fibers as the demineralized bone matrix material; or (iii) a solid demineralized plug or insert disposed in the perforations.

5. A bone implant according to claim 1, wherein the perforations comprise side walls each of which is surface demineralized.

6. A bone implant according to claim 5, wherein the perforations are partially filled with demineralized bone powder, demineralized bone fibers, demineralized bone plugs, or demineralized bone inserts.

7. A bone implant according to claim 5, wherein the plurality of perforations are spaced in a configuration to contact adjacent bone surfaces when the bone implant is implanted into a bone defect of a patient.

8. A bone implant according to claim 1, wherein the first surface and the second surface are coated with demineralized bone matrix material.

9. A bone implant according to claim 8, wherein (i) a depth of the demineralized region varies along the first surface and the second surface; (ii) the first surface and the second surface of the bone implant is demineralized so as to avoid subsidence when the bone implant is implanted into a facet joint of a patient; or (iii) the demineralized bone coating binds to the bone implant by air drying, freeze drying, heat drying, or by using a chemical cross-linking agent.

10. An allograft configured for disposal in a facet joint defect, the allograft comprising a first surface and a second surface, the first surface and the second surface comprising a demineralized bone matrix material and comprising a plurality of perforations having demineralized bone disposed therein; and a third surface facing the same direction as the first surface and the second surface of the allograft comprising nondemineralized cortical bone, wherein the third surface is disposed between the first surface and the second surface, and the allograft comprises a top surface and a bottom surface, the perforations extending from the top surface, through the demineralized bone matrix, to the bottom surface to provide channels between the top and the bottom surfaces; and the third surface of the nondemineralized cortical bone does not contain any perforations, wherein the top and the bottom surfaces comprise the first, the second and the third surfaces.

11. An allograft according to claim 10, wherein the perforations comprise a coating of demineralized bone powder, demineralized bone fibers, or a demineralized plug, or a demineralized insert.

12. An allograft according to claim 10, wherein the perforations comprise side walls each of which is surface demineralized.

13. An allograft according to claim 10, wherein the perforations are spaced in a configuration to contact adjacent bone surfaces when the allograft is implanted into the facet joint of a patient.

* * * * *

UNITED STATES PATENT AND TRADEMARK OFFICE
CERTIFICATE OF CORRECTION

Page 1 of 1

PATENT NO. : 10,172,651 B2
APPLICATION NO. : 13/660434
DATED : January 8, 2019
INVENTOR(S) : Emerton et al.

It is certified that error appears in the above-identified patent and that said Letters Patent is hereby corrected as shown below:

In the Specification

In Column 4, Line 53, delete ""A" and insert -- A --, therefor.

In Column 9, Line 62, delete "groves" and insert -- grooves --, therefor.

In Column 10, Line 41, delete "reminder" and insert -- remainder --, therefor.

In Column 13, Line 5, delete "polyglycolide (PG)," and insert -- polyglycolide (PGA), --, therefor.

In Column 15, Line 22, delete "SIGMA A6012." and insert -- SIGMA A6012). --, therefor.

In Column 21, Line 46, delete "CGTF-3," and insert -- CTGF-3, --, therefor.

In Column 21, Line 50, delete "and or" and insert -- and/or --, therefor.

In Column 22, Line 9, delete "(EP Appin." and insert -- (EP Appln. --, therefor.

In Column 22, Line 24, delete "sodium bisulfate, sodium bisulfate," and insert -- sodium bisulfate, sodium bisulfite, --, therefor.

Signed and Sealed this
Twenty-fifth Day of June, 2019

Andrei Iancu
*Director of the United States Patent and Trademark Office*